US012603156B2

(12) United States Patent
Jackson et al.

(10) Patent No.: US 12,603,156 B2
(45) Date of Patent: Apr. 14, 2026

(54) METHOD OF SYNTHESIZING A RADIOPHARMACEUTICAL

(71) Applicants: GE Healthcare Limited, Buckinghamshire (GB); General Electric Company, Schenectady, NY (US)

(72) Inventors: Alexander Jackson, Buckinghamshire (GB); Jonathan Robert Shales, Buckinghamshire (GB); David Alko Golden, Budapest (HU); Julian Grigg, Buckinghamshire (GB); Szilárd Németh, Budapest (HU)

(73) Assignee: GE Healthcare Limited, Buckinghamshire (GB)

( * ) Notice: Subject to any disclaimer, the term of this patent is extended or adjusted under 35 U.S.C. 154(b) by 804 days.

(21) Appl. No.: 17/043,210

(22) PCT Filed: Mar. 29, 2019

(86) PCT No.: PCT/EP2019/058110
§ 371 (c)(1),
(2) Date: Sep. 29, 2020

(87) PCT Pub. No.: WO2019/185931
PCT Pub. Date: Oct. 3, 2019

(65) Prior Publication Data
US 2021/0020271 A1 Jan. 21, 2021

(30) Foreign Application Priority Data
Mar. 29, 2018 (GB) ..................................... 1805283

(51) Int. Cl.
*G16C 20/10* (2019.01)
*A61K 51/00* (2006.01)
(Continued)

(52) U.S. Cl.
CPC ............ *G16C 20/10* (2019.02); *B01J 19/004* (2013.01); *G16C 20/20* (2019.02); *A61K 51/00* (2013.01)

(58) Field of Classification Search
None
See application file for complete search history.

(56) References Cited

U.S. PATENT DOCUMENTS

2014/0243500 A1* 8/2014 Engell .................... C07B 59/00
378/207
2018/0016296 A1 1/2018 Murphy et al.

FOREIGN PATENT DOCUMENTS

CN 103946851 7/2014
CN 103958445 7/2014
(Continued)

OTHER PUBLICATIONS

Claggett, S. B., Quinn, K. M., Lazari, M., Moore, M. D., & van Dam, R. M. (2013). Simplified programming and control of automated radiosynthesizers through unit operations. EJNMMI research, 3(1), 1-13. (Year: 2013).*
(Continued)

*Primary Examiner* — Karlheinz R. Skowronek
*Assistant Examiner* — Mary C Leverett
(74) *Attorney, Agent, or Firm* — Lathrop GPM LLP; Malaika O.D. Tyson

(57) ABSTRACT

The present invention relates a method of monitoring an automated radiosynthesizer during a run and the radiosynthesizer having a number of individual activity detectors operably associated therewith. The method comprises the steps of recording S10 activity data from each activity detector; accessing S20 historic data from a data storage; detecting S30 precursor of yield drop in the recorded activity data based on the historic data; predicting (S40 yield when synthesizing a tracer with the radiosynthesizer based on the (Continued)

detected precursor of yield drop; and initiating S50 actions related to a level of predicted yield.

17 Claims, 11 Drawing Sheets

(51) Int. Cl.
B01J 19/00 (2006.01)
G16C 20/20 (2019.01)

(56) References Cited

FOREIGN PATENT DOCUMENTS

| | | | | | |
|---|---|---|---|---|---|
| CN | 107635949 | | 1/2018 | | |
| JP | 2004279192 | A | 10/2004 | | |
| JP | 2015501462 | A | 1/2015 | | |
| WO | 2012024663 | A1 | 2/2012 | | |
| WO | 2013048954 | A1 | 4/2013 | | |
| WO | 2013049577 | A1 | 4/2013 | | |
| WO | WO-2018048873 | A2 | * | 3/2018 | ............. A61B 6/037 |

OTHER PUBLICATIONS

Boschi, S., Lodi, F., Malizia, C., Cicoria, G., & Marengo, M. (2013). Automation synthesis modules review. Applied radiation and isotopes, 76, 38-45. (Year: 2013).*
Srivastava, Suresh C., and Leonard F. Mausner. "Therapeutic radionuclides: production, physical characteristics, and applications." Therapeutic nuclear medicine. Berlin, Heidelberg: Springer Berlin Heidelberg, 2013. 11-50. (Year: 2013).*
Chochevska, Maja, et al. "Evaluation of factors with potential influence on [18F] FDG radiochemical synthesis yield." Applied Radiation and Isotopes 199 (2023): 110900. (Year: 2023).*
Amaraesekera, et al., "High-pressure, compact, modular radiosynthesizer for production of positron emitting biomarkers," Applied Radiation and Isotopes 78, Mar. 10, 2013, pp. 88-101.
Claggett, et al., "Simplifid programming and control of automated radiosynthesizers through unit operations," EJNMMI Research a SpringerOpen Journal, 2013, 14 pages.
German Search Report received in Application No. GB1805283.7 dated Nov. 30, 2018, 3 pages.

Lazari, et al., "Fully Automated Production of Diverse 18F-Labeled PET Tracers on the ELIXYS Multireactor Radiosynthesizer Without Hardware Modification," Downloaded from tech.snmjournals.org by European Patent Office on Nov. 7, 2019, 10 pages.
Lazari, Mark Saul, "Thinking inside the "box": Development and implementation of a novel automated radiosynthesizer for 18F-labeled positron emission tomography tracers," UCLA Electronic These and Dissertations, 2015, 238 pages.
Lindsey, Jonathan S., "A retrospective on the automation of laboratory synthetic chemistry," 8386 Chemometrics and Intelligent Laboratory Systems, 17 (1992) October, No. 1, Amsterdam, NE, 32 pages.
Notification of Transmittal of the International Search Report received in Application No. PCT/EP2019/058110 dated Nov. 18, 2019, 7 pages.
Written Opinion of the International Searching Authority received in Application No. PCT/EP2019/058110 dated Nov. 18, 2019, 9 pages.
Office Action received in Japanese Application No. 2020-552236 dated Dec. 20, 2022, with translation, 14 pages.
National Intellectual Property Administratoin, P.R. China, " First Office Action", issued in connection with Chinese Patent Application No. 201980035979.7, dated Mar. 21, 2024, 14 pages.
National Intellectual Property Administratoin, P.R. China, "Search Report", issued in connection with Chinese Patent Application No. 201980035979.7, dated Mar. 29, 2019, 2 pages.
Linyi et al., "Current Status and Prospects of Radiopharmaceutical for Diagnosis", Journal of Isotopes, vol. 30, No. 3, Nov. 30, 2017, pp. 292-306.
Japanese Office Action for Japanese Patent Application No. 2023-189090, dated May 22, 2025, including English translation.
Korea Intellectual Property Office, "Notice of Preliminary Rejection," regarding Application No. 10-2020-7030760, 27 pages, dated Jun. 20, 2024.
S. Claggett, et al., "Simplified programming and control of automated radiosynthesizers through unit operations," EJNMMI Research 2013, 3:53 http://www.ejnmmires.com/content/3/1/53, 13 pages, dated 2013.
S. Vallabhajosula, "Molecular Imaging: Radiopharmaceuticals for PET and SPECT," e-ISBN 978-3-540-76735-0, Springer-Verlag Berlin Heidelberg, dated 2009.
Japanese Patent Application No. 2023-189090 Office Action.

* cited by examiner

METHOD OF SYNTHESIZING A RADIOPHARMACEUTICAL

CROSS REFERENCE TO REPLATED APPLICATIONS

This application is a filing under 35 U.S.C. § 371 of international application number PCT/EP2019/058110, filed Mar. 29, 2019, which claims priority to application number GB 1805283.7 filed on Mar. 29, 2018, the entire disclosures of each of which are hereby incorporated by reference.

TECHNICAL FIELD

The present invention relates to the field of radiopharmaceuticals during the synthesis thereof, such as radiopharmaceuticals used in Positron Emission Tomography (PET) and Single-Photon Emission Computed Tomography (SPECT).

BACKGROUND

PET and SPECT imaging systems are increasingly used for detection of diseases and are useful in providing early detection and a definite diagnosis for such diseases (e.g., disease states within oncology and neurology). For example, currently, a large percentage of PET and SPECT tests are related to cancer detection and early Alzheimer detection. These diseases require early diagnosis to allow a timely and effective treatment.

PET and SPECT imaging systems create images based on the distribution of positron-emitting isotopes and gamma emitting isotopes, respectively, in the tissue of a patient. The isotopes are typically administered to a patient by injection of radiopharmaceuticals including a probe molecule having a positron-emitting isotope, e.g., carbon-11, nitrogen-13, oxygen-15, or fluorine-18, or a gamma radiation emitting isotope, e.g. technetium-99m. The radiopharmaceutical is readily metabolized, localized in the body or chemically binds to receptor sites within the body. Once the radiopharmaceutical localizes at the desired site (e.g., chemically binds to receptor sites), a PET or SPECT image is generated.

Examples of known radiopharmaceuticals include $^{18}$F-FLT ([$^{18}$F]fluorothymidine), $^{18}$F-FDDNP (2-(1-{6-[(2[$^{18}$F]fluoroethyl)(methyl)amino]2-naphthyl}ethylidene)malonitrile), $^{18}$F-FHBG (9-[4[$^{18}$F]fluoro-3-(hydroxymethyl)butyl]guanine or [$^{18}$F]-penciclovir), $^{18}$F-FESP ([$^{18}$F]-fluoroethylspiperone), $^{18}$F-p-MPPF (4-(2-methoxyphenyl)-1-[2-(N-2-pyridinyl)-p-[18p]fluorobenzamido]ethylpiperazine) and $^{18}$F-FDG ([$^{18}$F]-2-deoxy-2-fluoro-D-glucose).

Radioactive isotopes in radiopharmaceuticals are isotopes exhibiting radioactive decay, for example, emitting positrons. Such isotopes are typically referred to as radioisotopes or radionuclides. Exemplary radioisotopes include $^{18}$F, $^{124}$I, $^{11}$C, $^{13}$N and $^{15}$O, which have half-lives of 110 minutes, 4.2 days, 20 minutes, 10 minutes, and 2 minutes, respectively.

Because radioisotopes have such short half-lives, the synthesis and purification of the corresponding radiopharmaceutical must be rapid and efficient. Any quality control (QC) assessments on the radiopharmaceutical must also take place in a short period of time. Preferably, these processes (i.e., synthesis, purification, and QC assessment) should be completed in a time well under the half-life of the radioisotope in the radiopharmaceutical. Presently, QC assessments (e.g., chemical yield and chemical purity) may be relatively slow mainly due to the fact that they are conducted manually. Accordingly, there is a need for systems, components, and methods for capturing, analysing, and interpreting data obtained during the synthesis and purification processes of a radiopharmaceutical to ensure that those synthesis and purification are proceeding efficiently to produce quality radiopharmaceuticals in a desired quantity. From this analysis, changes can be implemented before, during or after the synthesis and/or purification of the radiopharmaceutical to correct any deficiencies, as they occur during the radiopharmaceutical's synthesis.

A drawback with present solutions is that a "bad" batch (having low yield) is detected using absolute plateau values when it has occurred. Thus, the user has no possibility to initiate actions to prevent a drop in yield during a process run.

SUMMARY

An object of the present disclosure is to provide methods and devices configured to execute methods and computer programs which seek to mitigate, alleviate, or eliminate one or more of the above-identified deficiencies in the art and disadvantages singly or in any combination.

The object is achieved by a method of monitoring an automated radiosynthesizer during a run. The radiosynthesizer has a number of individual activity detectors operably associated therewith and the method comprising the steps of recording activity data from each activity detector; accessing historic data from a data storage; detecting precursors of yield drop in the recorded activity data based on historic data; predicting yield when synthesizing a tracer with the radiosynthesizer based on the detected precursors of yield drop; and initiating actions related to a level of predicted yield.

An advantage is that a higher level of yield may be provided since unexpected yield drops are avoided.

The object is also achieved by a control system for monitoring an automated radiosynthesizer during a run, wherein the radiosynthesizer has a number of individual activity detectors operably associated therewith. The control system is configured to recording activity data from each activity detector; detecting precursors of yield drop in the recorded activity data based on historic data accessible from a data storage; predicting yield when synthesizing a tracer with the radiosynthesizer based on the detected precursors of yield drop; and recommending actions related to a level of predicted yield.

Further objects and advantages may be obtained from the detailed description by a skilled person in the art.

DETAILED DESCRIPTION

Figure 1:
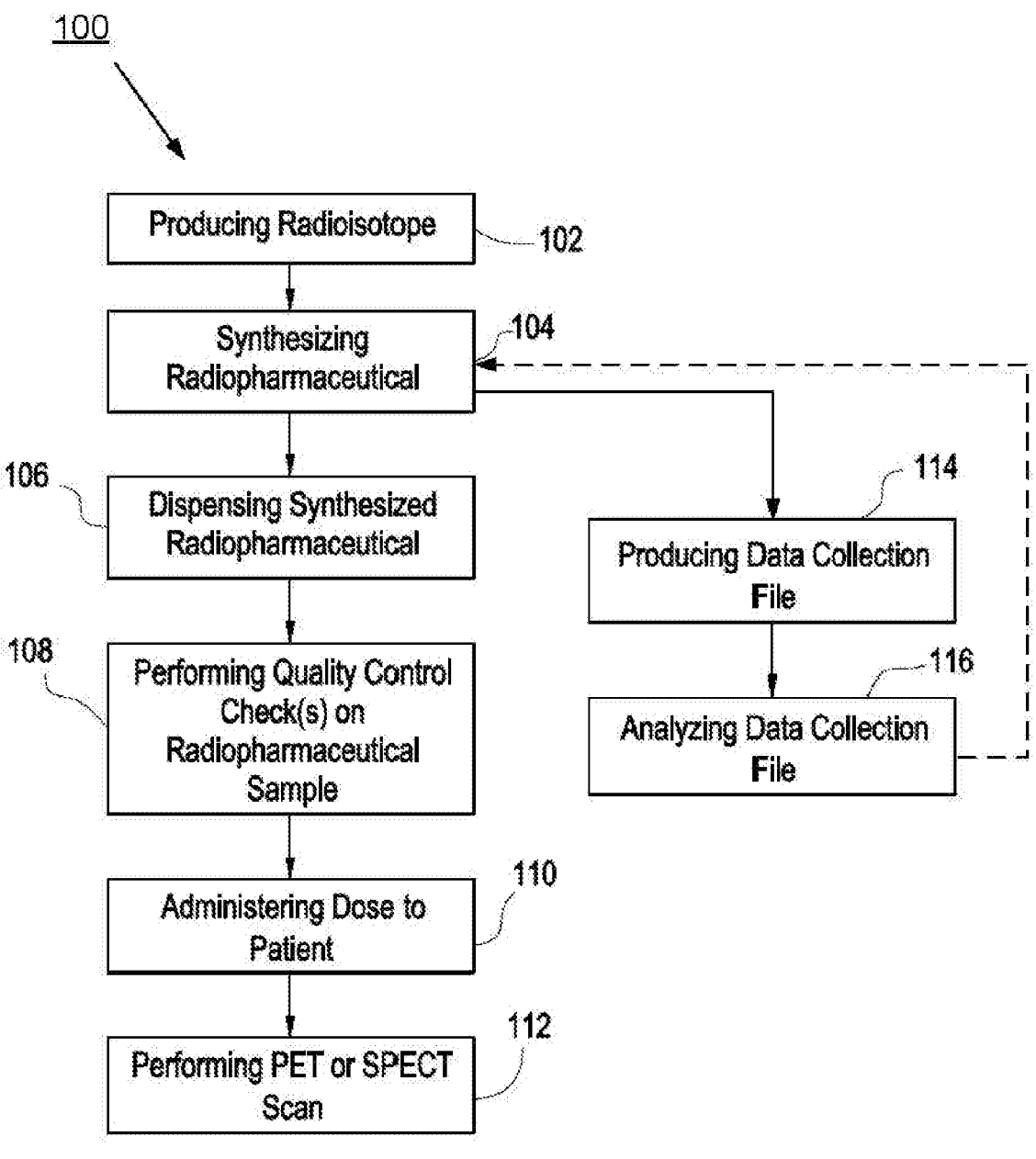
FIG. 1 illustrates a method for producing and using a PET or SPECT imaging agent and extracting data collection file data according to an exemplary embodiment of the invention.

It will be readily understood by those persons skilled in the art that the embodiments of the inventions described herein are capable of broad utility and application. Accordingly, while the invention is described herein in detail in relation to the exemplary embodiments, it is to be understood that this disclosure is illustrative and exemplary of embodiments and is made to provide an enabling disclosure of the exemplary embodiments. The disclosure is not intended to be construed to limit the embodiments of the invention or otherwise to exclude any other such embodiments, adaptations, variations, modifications and equivalent arrangements.

The following descriptions are provided of different configurations and features according to exemplary embodiments of the invention. These configurations and features may relate to providing systems and methods for quality control of radiopharmaceuticals and other compounds or formulations containing radioisotopes. While certain nomenclature and types of applications or hardware are described, other names and application or hardware usage is possible and the nomenclature provided is done so by way of non-limiting examples only. Further, while particular embodiments are described, these particular embodiments are meant to be exemplary and non-limiting and it further should be appreciated that the features and functions of each embodiment may be combined in any combination as is within the capability of one of ordinary skill in the art.

The figures depict various functionality and features associated with exemplary embodiments. While a single illustrative block, sub-system, device, or component is shown, these illustrative blocks, sub-systems, devices, or components may be multiplied for various applications or different application environments. In addition, the blocks, sub-systems, devices, or components may be further combined into a consolidated unit. Further, while a particular structure or type of block, sub-system, device, or component is shown, this structure is meant to be exemplary and non-limiting, as other structure may be able to be substituted to perform the functions described.

Exemplary embodiments of the invention relate to automated synthesis systems for radiopharmaceuticals, such systems also referred to and used herein as 'synthesizers' or 'radiosynthesizers'. The term 'automated' denotes that the synthesizer is programed to cause performance of certain steps in the radiosynthesis operation for producing a tracer. The synthesis system may produce radiopharmaceuticals for use with either PET or SPECT scanners. For example, the synthesis system may be the FASTlab™ system from GE Healthcare, Liege, Belgium. The use of the FASTlab system in examples described herein is meant to be exemplary and non-limiting. It should be appreciated that the embodiments described herein may be used with a variety of synthesis systems manufactured by companies other than GE Healthcare. It should further be appreciated that the use of the term "radiopharmaceutical", "radiotracer", "PET tracer", or "SPECT tracer" herein is meant to be exemplary and non-limiting and the mention of one term does not exclude substitution of the other terms in the described embodiment. Additionally, the term "activity detector" refers to a detection instrument incorporated into an automated synthesizer which detects radioactivity from the gamma source, e.g., the positron-emitting isotope, in the vicinity thereof. Such activity detectors are well known in the art.

The present disclosure relates to automated synthesis of radiopharmaceuticals by monitoring the radiosynthesizer during a run and detecting precursors of yield drop in activity data recorded by activity detectors associated with the radiosynthesizer. The precursors of yield drop is used to predicting yield when synthesizing a tracer in the radiosynthesizer and dependent on the level of predicted yield actions are recommended to improve or maintain yield. Since performance variations have been observed for an automated synthesis device, such as a FASTlab synthesizer, at different local manufacturing/synthesis sites, the present invention provides a method for ensuring that synthesis at each synthesis device is optimized for its production runs. The present disclosure thus provides a method for monitoring radiosynthesis with an automated radiosynthesizer and recommending action when precursors of yield drop has been detected, where the radiosynthesizer includes one or more activity detectors associated therewith.

All chemistry processes that emit radiation are contemplated by embodiments disclosed herein including, but not limited to, nuclear and fluorescent, for example. With respect to nuclear applications, embodiments include, but are not limited to, medical isotopes and corresponding radiation properties such as $^{18}$F, $^{11}$C, $^{14}$C, $^{99m}$TC, $^{123}$I, $^{125}$I, $^{131}$I, $^{68}$Ga, $^{67}$Ga, $^{15}$O, $^{13}$N, $^{82}$Rb, $^{62}$Cu, $^{32}$P, $^{89}$Sr, $^{153}$Sm, $^{186}$Re, $^{210}$Tl, $^{111}$In, or combinations thereof. Preferred isotopes include those used for PET such as $^{18}$F, $^{11}$C and $^{68}$Ga.

FIG. 1 depicts a flow chart of a method of synthesizing and using a PET or SPECT imaging agent and extracting data collection file data according to an exemplary embodiment of the invention. The method 100 as shown in FIG. 1, may be executed or otherwise performed by one or a combination of various systems, components, and sub-systems, including a computer implemented system. Each block shown in FIG. 1 represents one or more processes, methods, and/or subroutines carried out in the exemplary method 100.

At block 102, a radioisotope is produced. The radioisotope (e.g., $^{18}$F or $^{11}$C) is typically produced using a cyclotron (e.g., GE PETtrace 700 cyclotron) for PET radioisotopes or using a generator for SPECT radioisotopes (e.g., to produce the $^{99m}$Tc). The cyclotron or generator may be located at a manufacturing site or it may be located in proximity to the scanner. Locating the cyclotron or generator on-site with the PET or SPECT scanner minimizes transportation time for the radioisotope. It should be appreciated that while "PET" and "SPECT" are referred to herein such examples are exemplary and the mention of one does not preclude application to the other.

At block 104, a radiopharmaceutical is synthesized using the radioisotope. A synthesizer is used to combine the radioisotope with a radioligand. The result is a radiopharmaceutical.

The synthesizer may be manually operated, semi-automated in operation, or fully automated. For example, the GE Healthcare FASTlab system is a fully automated synthesizer. The synthesizer is generally operated in a "hot cell" to shield the operator from the radioactivity of the radioisotope. During the synthesis of the radiopharmaceutical, data can be collected during the process. The data corresponds to radio detector or sensor measurements at various points in the synthesis process. The data are collected at various time intervals and may be electronically stored. The data may be output or saved in the form a data collection file. The synthesizer may employ a cassette which is mated thereto and contains the various reagents and other equipment, such as syringe pumps and vials, required for the synthesis of the radiopharmaceutical. The cassette may be removable and disposable. Cassettes may be configured to support the synthesis of one or more radiopharmaceuticals.

At block 106, the synthesized radiopharmaceutical is dispensed. The doses of the radiopharmaceutical are dispensed into collecting vials for patient administration and for QC. A sample of the bulk synthesized radiopharmaceutical may be dispensed directly into a QC system and/or cassette for QC testing. Systems and methods of QC testing are shown in PCT Appl. No. US11/2011/048564 filed on Aug. 22, 2011, the contents of which are incorporated herein by reference in their entirety.

At block 108, quality control checks on a radiopharmaceutical sample are performed. There may be one or more QC checks performed. These QC checks may be automated. The QC system may include a cassette having a plurality of components for performing the tests. The cassette may be configured for insertion into a QC system to carry out the QC checks. The QC system may be a stand-alone system or it may be integrated with the synthesizer described above. Radiopharmaceutical doses are dispensed from the synthesizer. Sample(s) from one or more dispensed vials may be selected for QC checks. These samples may be sent to the QC system. Alternatively, the QC system may be connected or coupled to the synthesizer such that an appropriate sample may be directly output from the synthesizer to the QC system.

At block 110, a dose from the same production batch as the sample on which the QC tests were conducted is administered to a patient.

At block 112, a PET or SPECT scan is performed on the patient who received the dose.

At block 114, a data collection file is produced from the synthesizer. This file contains data collected during the radiopharmaceutical synthesis. The data collection file may be formatted and contain data as described herein. Alternatively, other formats for the file may be used. For example, the file may be a log file such as produced by the GE Healthcare FASTlab system as described above. The use of the term "data collection file" or "log file" herein is meant to be exemplary and non-limiting, as there are other terms that may be used for such a data collection file with data collected during a radiopharmaceutical process. It should be appreciated that the data collection file may be produced at any point during the synthesis process.

The data collection file may be produced in hard copy format and/or may be stored electronically. For example, the data collection file may be printed by an output device communicatively coupled to the synthesizer, such as a printer. Alternatively, the data collection file may be output or stored in an electronic format. For example, the synthesizer may have an electronic display or be coupled to a computer system for displaying the data collection file in an electronic format. The data collection file may be electronically saved using electronic storage, either internal to the synthesizer or external thereto. For example, the synthesizer may have solid state storage, both temporary, such as random access memory and/or more permanent such as flash memory or hard disk type storage.

Information (indicated by a dashed line) from step 116 is used in the synthesizing of radiopharmaceuticals 104, and illustrates, for the sake of illustration and not of limitation, single batch diagnostics, 'yield advisor', or batch browser processing, as more fully described herein.

Figure 10:
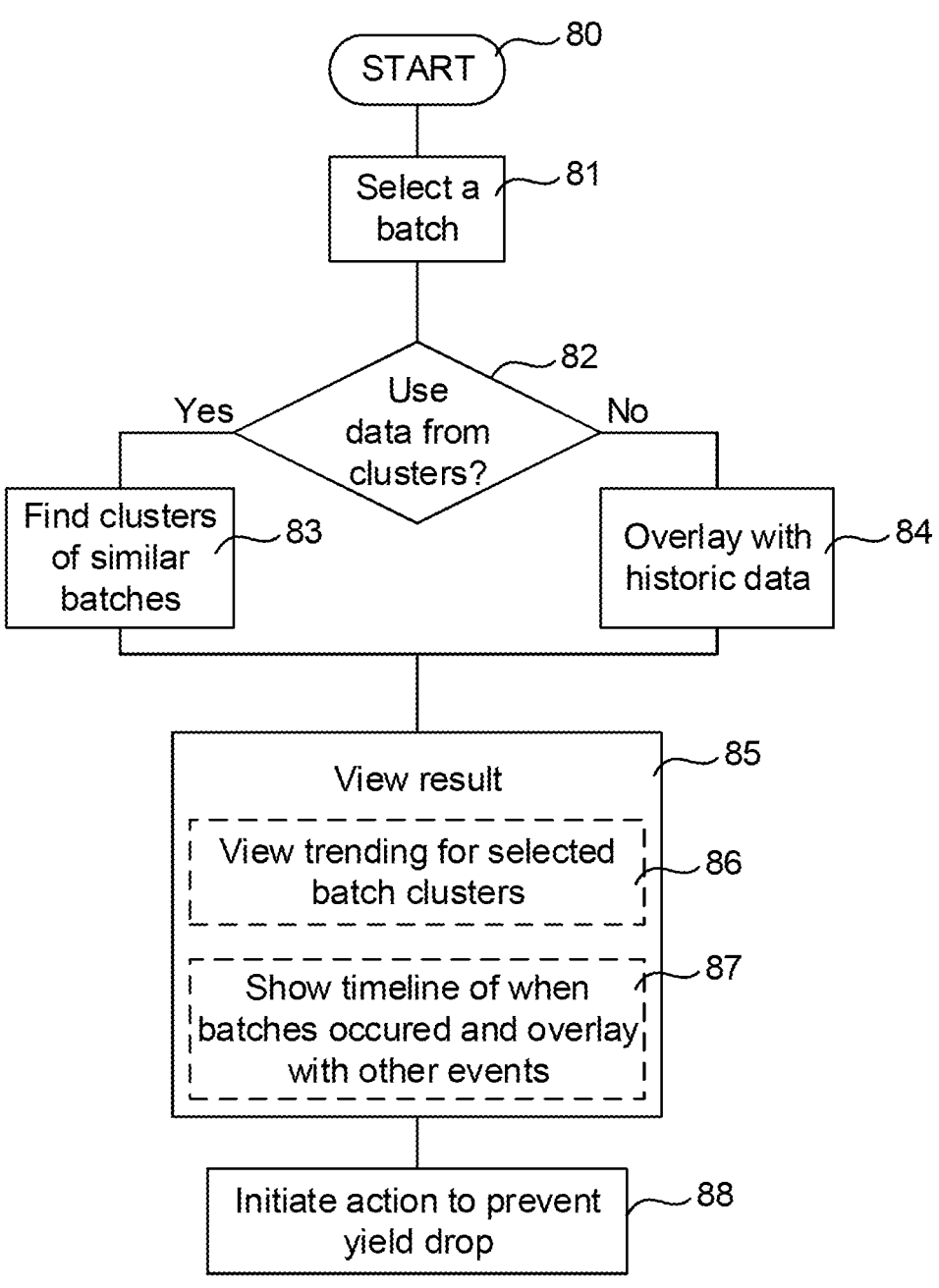
FIG. 10 illustrates a flowchart of a batch browser process.
Figure 11:
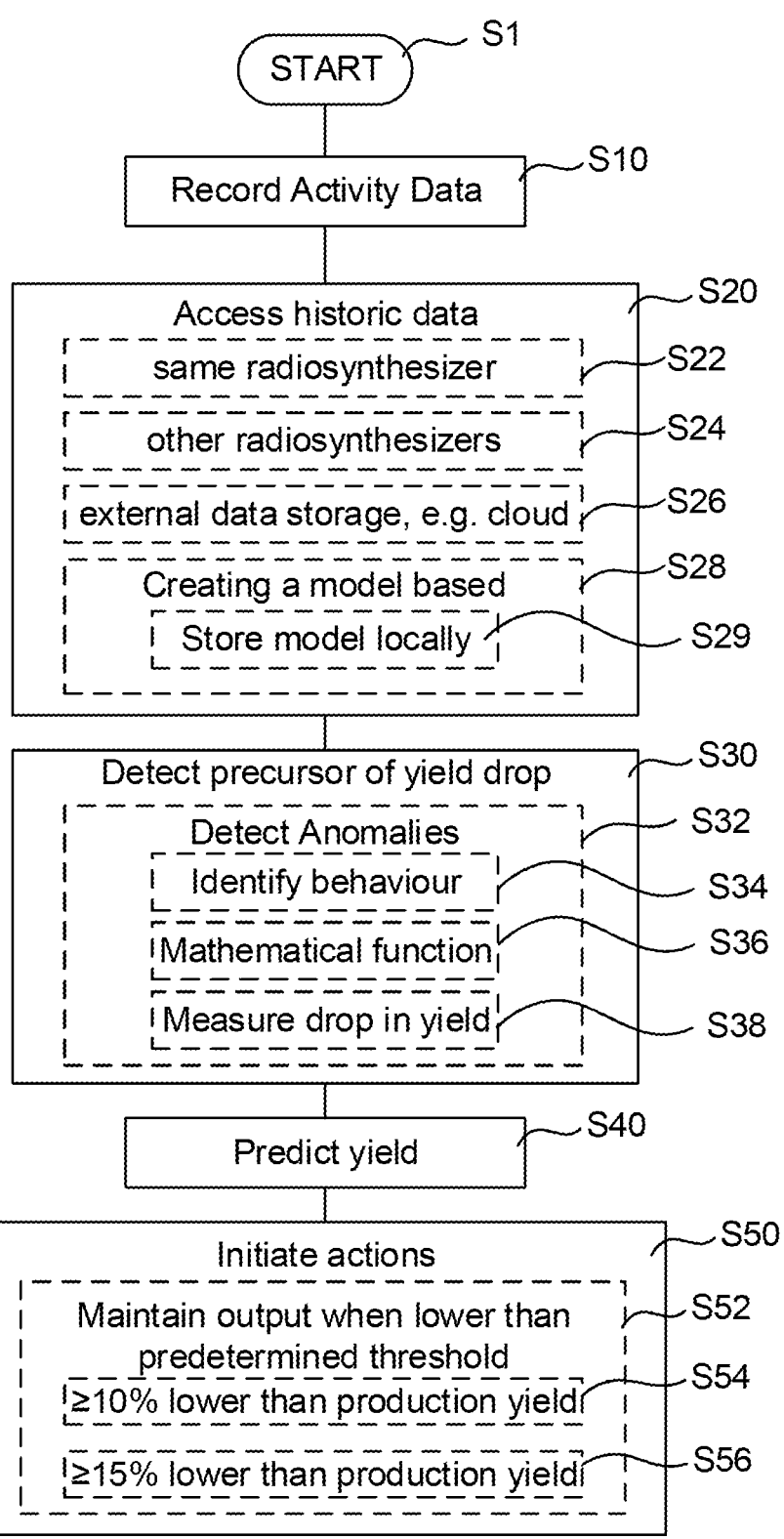
FIG. 11 illustrates a flowchart for monitoring an automated radiosynthesizer during a run.

FIGS. 10 and 11 are specific/alternate embodiments of step 116 from FIG. 1.

It should also be appreciated that the synthesizer may have input devices to allow for user interaction with the system. These input devices may be communicatively coupled to the system. For example, the synthesizer may have a QWERTY or equivalent type keyboard, an alphanumeric pad, and/or a pointing input device. Combinations of input devices are possible. The synthesizer may be communicatively coupled to a computer network. For example, the synthesizer may be communicatively coupled to a local area network or similar network. Through such a network connection, the synthesizer may be communicatively coupled to one or more external computers, computer systems, and/or servers. In some embodiments, the synthesizer may be communicatively coupled to the Internet. The synthesizer may be wirelessly connected to the computer network or may be connected by a wired interface. The synthesizer may transmit and receive data over the computer network. For example, the data collection file may be transmitted over the computer network to another computer system or server. This other computer system or server may be remotely located at a geographically separate location from the synthesizer.

Furthermore, the synthesizer may be computer implemented such that synthesizer includes one or more computer processors, power sources, computer memory, and software. As stated above, the synthesizer may be communicatively coupled to one or more external computing systems. For example, the synthesizer may be communicatively coupled through a computer network, either wired or wireless or a combination of both, to an external computer system. The external computer system may provide commands to cause the synthesizer to operate as well as collect and analyze data from the data collection file. This combination of computer hardware and software may enable to the synthesizer to automatically operate and to perform certain collection of data, analysis of the data, and implementation of corrections or factors derived from the data.

At block 116, the data collection is analyzed. In accordance with exemplary embodiments, the data collection file is analyzed as described herein. As part of the analysis, certain factors and information may be gleaned from the data collection file. Using these factors and information, the radiopharmaceutical process may be altered, modified, and/or tuned. For example, the data analysis may determine that the process is not operating efficiently because a low yield is indicated. By way of non-limiting example, this may be indicative of a problem in the reaction vessel. A fix or modification may be implemented. Such a fix or modification may be manually applied by an operator or may be implemented automatically by the synthesizer based on command issued through a computer system. In some embodiments, the system may be completely automatic and no outside intervention is needed to perform an analysis and implement a correction or modification to the process.

Figure 2:
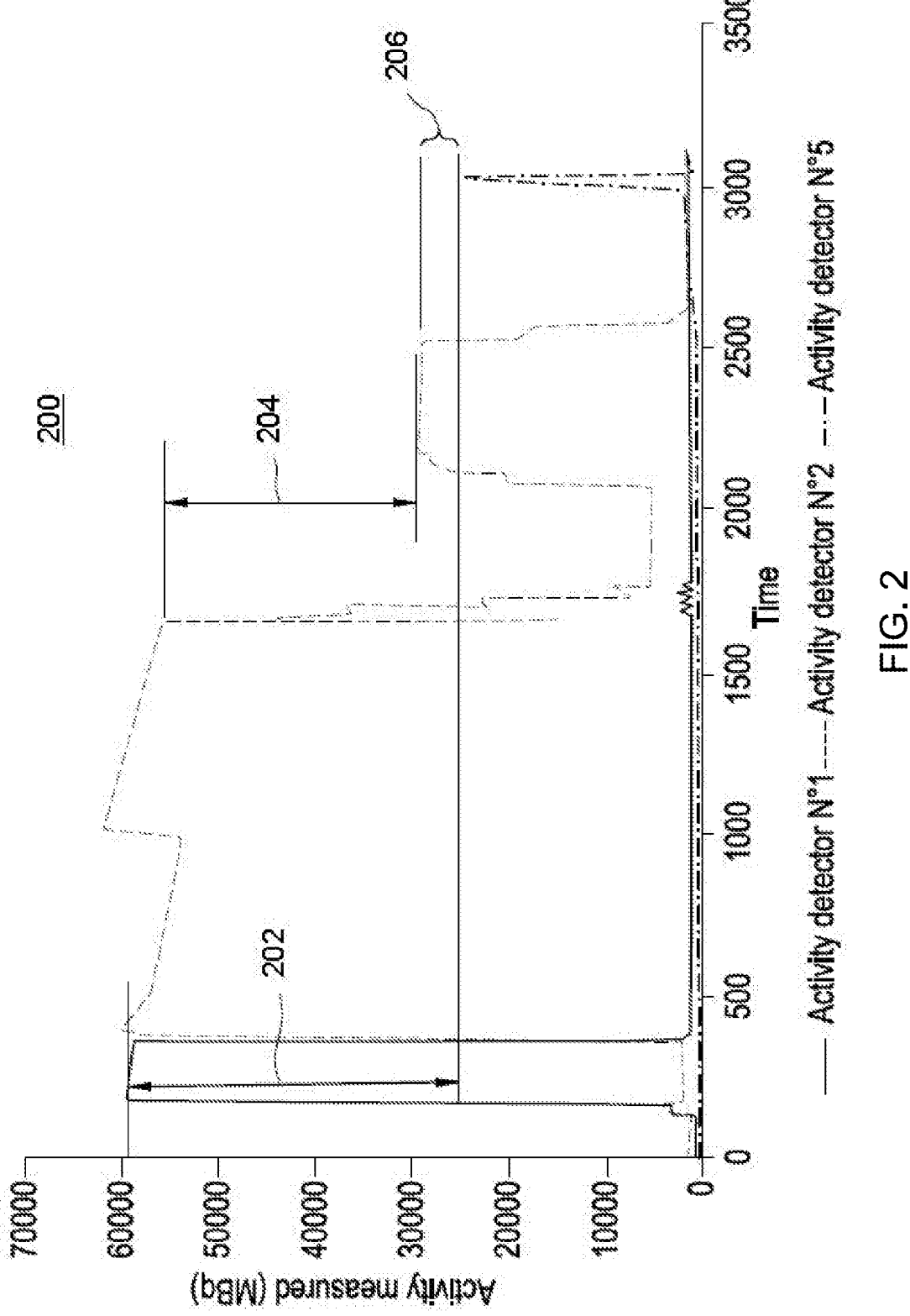
FIG. 2 illustrates a plot of data collection file data showing the yield steps according to an exemplary embodiment.

FIG. 2 depicts a graph showing how certain information, specifically yield information, can be gleaned from the data collection file data according to an exemplary embodiment. FIG. 2a is a representative trace of the radiosynthesis of FBA and flucliclatide, and graph 200 depicts a plot with an overlay of the components of the radiopharmaceutical synthesis process. The overall yield 202 is the sum of the first yield step 204 and the second yield step 206. These yield values can be used to assess the performance of the overall process, as well as identify problem areas of the process. According to exemplary embodiments, an exemplary or "standard" process with an exemplary yield may be determined for the system. The resulting data collected during the exemplary process, e.g., the measurements of the Activity Detectors, is plotted. The yield can be determined as shown in FIG. 2.

According to exemplary embodiments, Activity Detector No. 1 is positioned in the vicinity of the quaternary methyl ammonium (QMA) cartridge, Activity Detector No. 2 is positioned in the vicinity of the Reactor Vessel, and Activity Detector No. 5 is positioned in the vicinity of the outlet of the process that leads to a syringe or a production collection vial.

This resulting plot may form an exemplary "fingerprint" for the system. Subsequent runs made using the system can then be compared to this exemplary process. Deviations from the fingerprint can be noted through plots of the data collection file data as described above. From analysis of the plots in this comparison, problems with the system and its process may be readily identified and subsequently corrected. According to exemplary embodiments, if a trace is taken to be the fingerprint of a process that is optimal, a subsequent trace (e.g., from a subsequent synthesis run or from an instrument at a different site) can be compared to it. If the fingerprint of the subsequent trace varies significantly (e.g., more than 2%; more than 5%; more than 10% or more than 15%) in any region (e.g., the region that is covered by detectors 1, 2 or 5), the operator (or the synthesizer automatically) can diagnose the step of the synthesis that is not proceeding properly. According to exemplary embodiments, variations in the first yield step 204 and the second yield step 206 can be used to identify where in the process a problem may be occurring, either at the labelling step that forms [$^{18}$F]benzaldehyde (FBA); the conjugation step that forms [$^{18}$F]fluciclatide; or with any purification step involved in the synthesis process.

Figure 3:
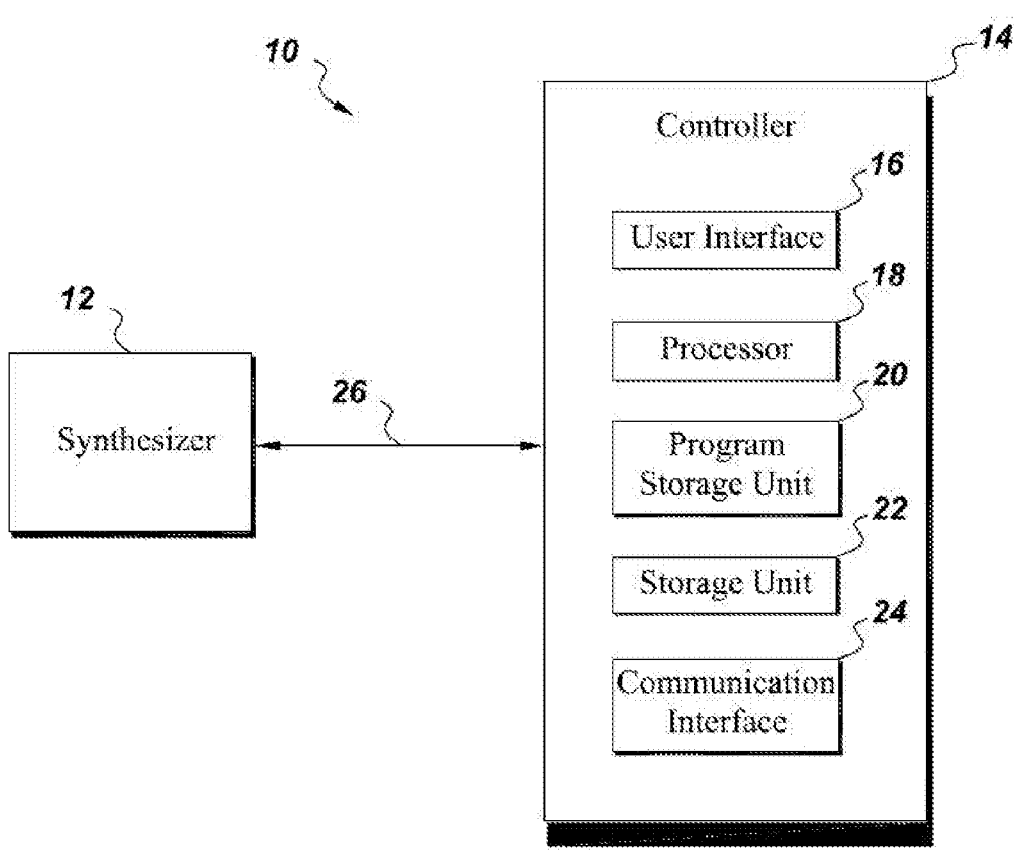
FIG. 3 is a diagrammatical view of a system for monitoring radiopharmaceutical production according to an exemplary embodiment.
Figure 4:
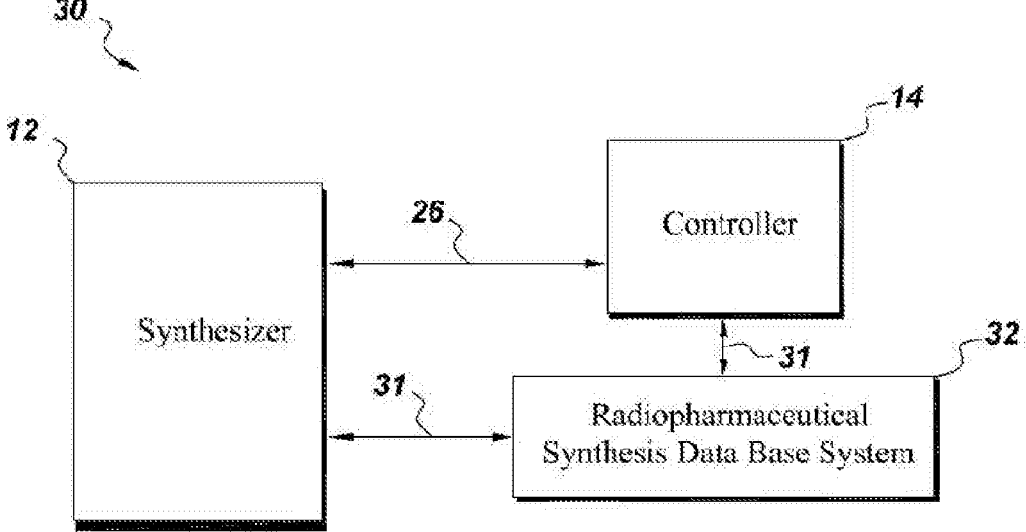
FIG. 4 is a diagrammatical view of sensor array according to an exemplary embodiment.

Referring to FIG. 3, a block diagram is shown that provides an overview of a radiopharmaceutical synthesis system. The system 10 includes a synthesizer 12 and a controller 14 having a user interface 16, a processor 18, a program storage unit 20, a storage unit 22, and a communication interface 24. The synthesizer 12 may be any suitable radiopharmaceutical synthesizer such as the FASTlab™ sold by GE Healthcare, for example. The synthesizer 12 contains actuators, sensors and a communication system to execute synthesis runs on a cassette/cartridge/chip and measure hardware parameters and sensor outputs which are transmitted to the controller 14. The synthesizer 12 communicates with the controller 14 via a network, including, but not limited to, a Local Area Network (LAN) 26. Any suitable network arrangement can be implemented to provide for communication between the synthesizer 12 and the controller 14 including, but not limited to a wide area network or WAN, such as the Internet. The program storage unit 20 stores radiopharmaceutical synthesizer process programs for synthesizing various radiopharmaceuticals, respectively, as well as other programs as necessary. The storage unit 22 stores information such as, but not limited to, reference values/value ranges for the various sensors in the synthesizer 12, respectively, in addition to synthesis run data output by the sensors during a synthesis run. Each radiopharmaceutical synthesized by the synthesizer 12 will have an associated set of reference values/value ranges for corresponding sensors. These reference values/value ranges can be considered as a "reference fingerprint" of the particular radiopharmaceutical synthesis process and/or cassette. The reference values/value ranges can be programmed into the controller 14 and updated periodically as necessary. The controller 14 and the synthesizer 12 can also receive reference values/value ranges periodically from a radiopharmaceutical synthesis data base system 32 via network 31, such as the Internet, for example, as shown in FIG. 4. The system 32 can be maintained on a local or global database system, on a CD, DVD, USB, or some other storage and processing arrangement. Any suitable communication arrangement can be implemented.

As previously noted, each acquired or measured data can be considered an acquired "fingerprint." This acquired fingerprint obtained during synthesis runs can be fed into a Failure Modes and Effects Analysis (FMEA), a storage device, or some other comparable quality assurance system, for example, which is maintained on a local and/or global database with potentially multiple contributing hospitals, users and research institutions, for example. In some embodiments, the FMEA can be maintained in the radiopharmaceutical synthesis data base system 32. The controller 14 may reside within the synthesizer 12 or in a remote location. In the current embodiment, the synthesizer 12 includes a controller (not shown) to process the commands and data supplied from controller 14 and the information provided by the radiopharmaceutical synthesis data base system 32. In some embodiments, the controller 14 can be arranged to initiate the real-time synthesis monitoring process and the controller (not shown) within the synthesizer can run the monitoring program.

Figure 5A:
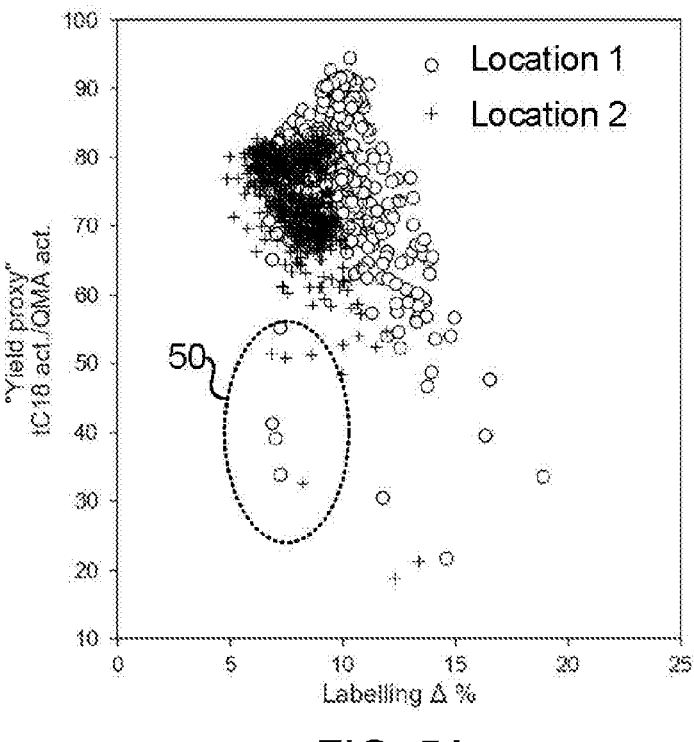
FIGS. 5*a* and 5*b* illustrate yield proxy as a function of Labelling α % and Activity loss at tC18, respectively.

In FIG. 5*a*, yield proxy for tC18 activity in relation to QMA activity is presented (where 100% yield is the desired result) as a function of labelling Δ (delta), measured in %. This parameter is defined in FIG. 6*b* and relates to the drop in yield during labelling. From FIG. 5*a*, which presents results from many runs at two different locations (Location 1 and Location 2) it is apparent that there is a correlation between yield and Δ% during labelling. Outliers, indicated by 50 indicate different failure modes and is a precursor of yield drop. Yield is predicted based on the precursor of yield drop and suitable actions may recommended to maintain or improve yield. However, the recommended action, exemplified below, is related to a level of predicted yield.

Figure 5B:
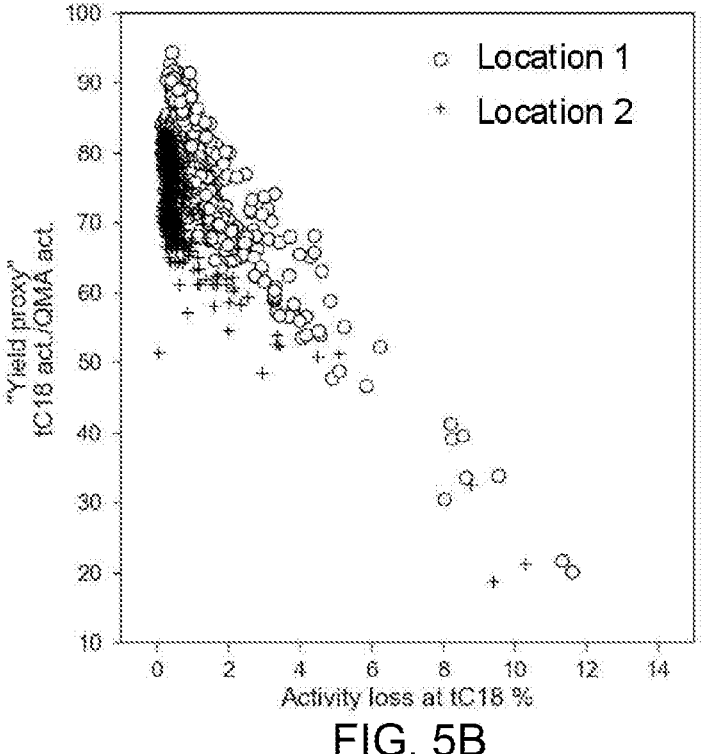
Figure 7A:
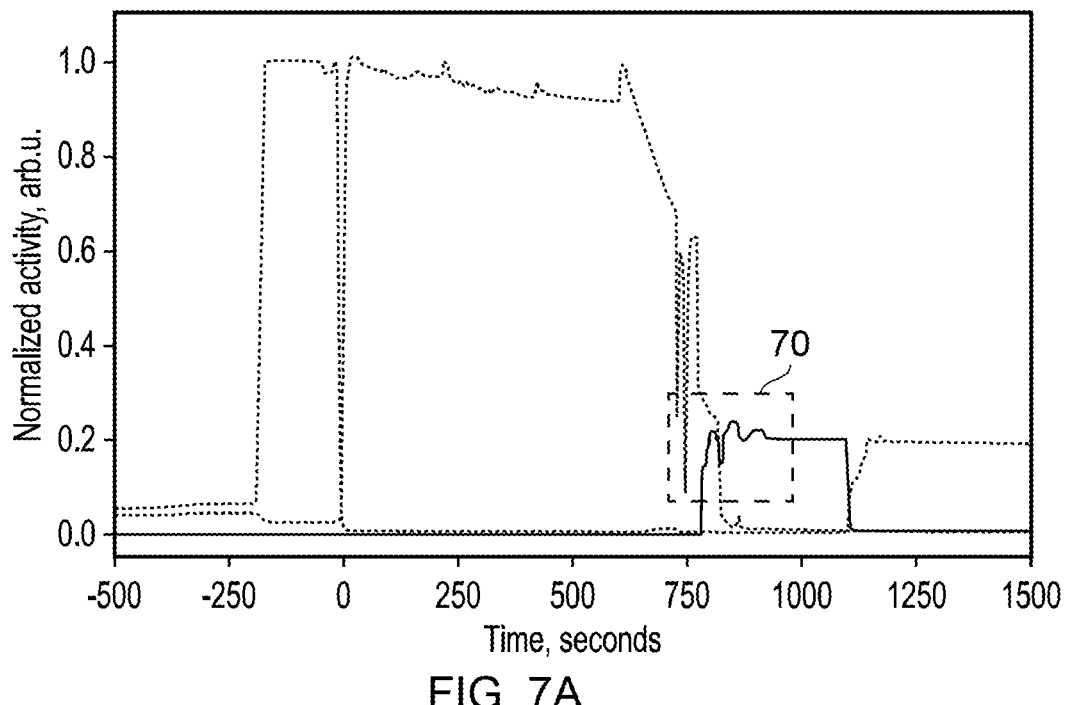
FIGS. 7*a* and 7*b* illustrate precursor events during trapping of FTAG on tC18 cartridge after labelling.
Figure 7B:
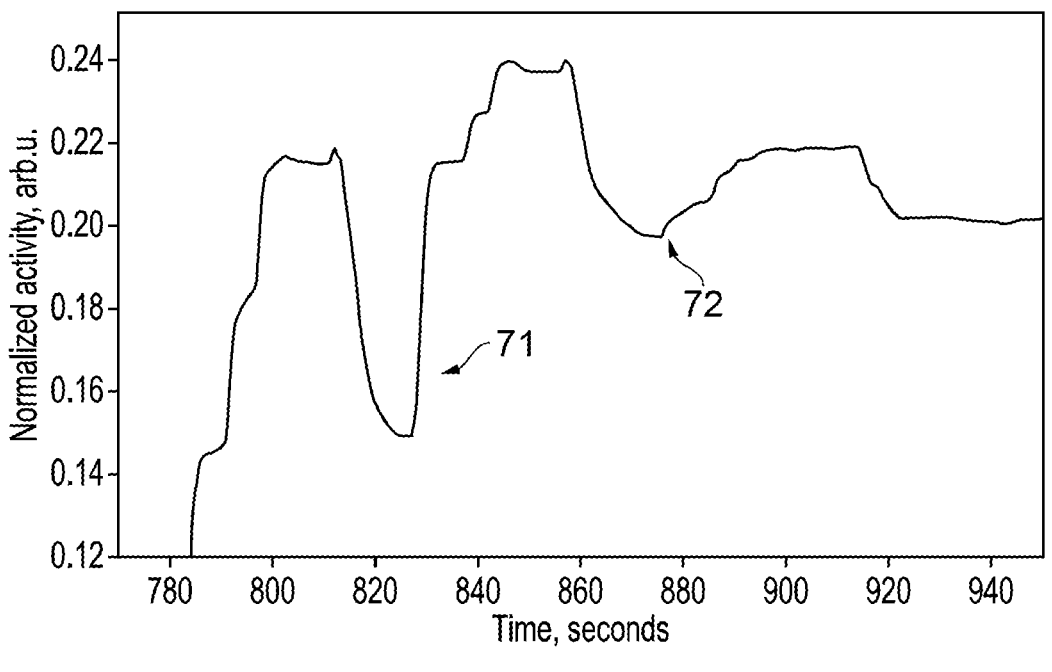

In FIG. 5*b*, yield proxy for tC18 activity in relation to QMA activity is presented (where 100% yield is the desired result) as a function of Activity loss at tC18, measured in %. This parameter is defined in FIG. 7*b* and relates to the activity loss during trapping. From FIG. 5*b*, which presents results from many runs at two different locations (Location 1 and Location 2) it is apparent that there is a strong correlation between yield and activity loss at tC18. High tC18 loss usually indicates sub-optimal labelling, causing low yield, and high tC18 loss a precursor of yield drop. As mentioned above, yield is predicted based on the precursor of yield drop and suitable actions may recommended to maintain or improve yield. However, the recommended action, exemplified below, is related to a level of predicted yield.

Figure 6A:
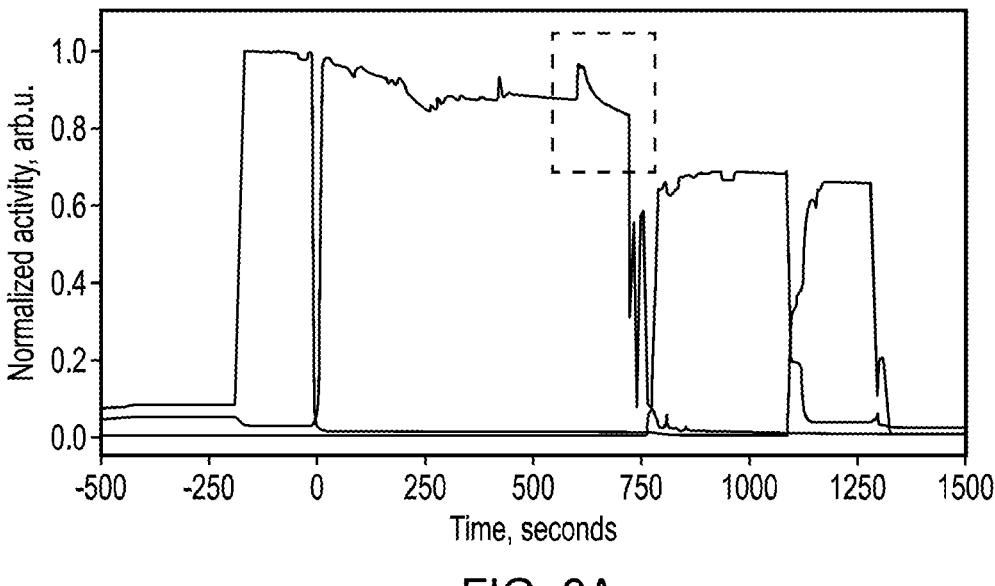
FIGS. 6*a*-6*c* illustrate precursor events during labelling reaction.
Figure 6B:
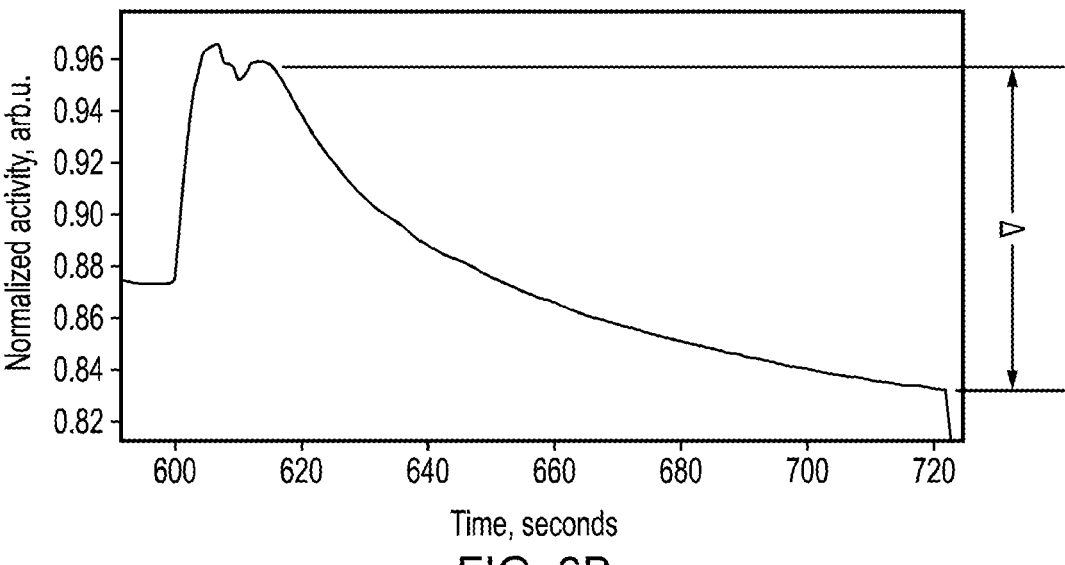

FIGS. 6*a* and 6*b* illustrate precursor events during labelling reaction. FIG. 6*a* illustrate a plot of data collection file data, similar to FIG. 2, showing a normalized activity as a function of time. Different activity sensors are used, as described in connection with FIG. 2, to create the graph. In a region of the graph, denoted 60, labelling occurs, and this section is shown in greater detail in FIG. 6*b*. The drop in normalized activity during labelling is a measure of yield drop and is denoted labelling Δ (delta), normally measured in %. As mentioned above, the yield drop during labelling is an example of a precursor of yield drop.

According to some embodiments, the step of detecting precursors of yield drop comprises detecting anomalies. The step of detecting anomalies may comprises measuring a drop in yield in the selected region as described above. Anomalies may also be detected by processing historic data from multiple earlier runs to identify behaviour that give an early warning signal for yield. In order to be able to compare historic data from different runs, the step of processing historic data may further comprises normalizing data from the multiple earlier runs on particular points. According to some embodiments, the step of detecting anomalies comprises fitting a mathematical function to a selected region and evaluating the mathematical function based on its behaviour. In this example the region 60 is the labelling reaction and by evaluating historic data it has been identified that the mathematical function for this region 60 is selected to be:

$$y = 1 - Ae^{-\lambda t},$$

wherein y is the yield, A and λ are constants and t is time, and the evaluation is based on the magnitude of λ.

Figure 6C:
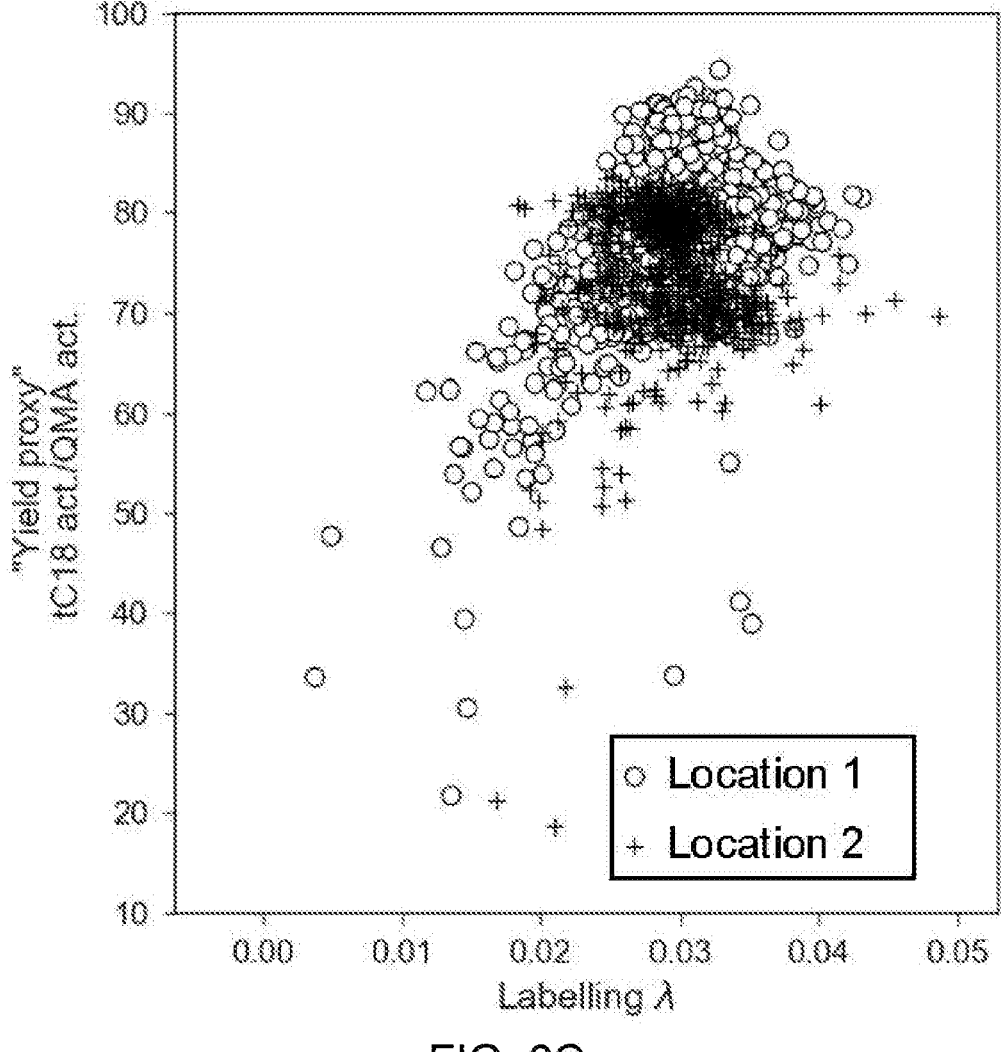

A large λ corresponds to a "strong curve", which is equal to a "normal" batch having a good yield. Thus a small λ corresponds to a low yield. FIG. 6c is a graph illustrating labelling λ as a function of yield proxy.

From historic data, many correlations may be identified between yield and data from the activity detectors. Another example is shown in connection with FIGS. 7a and 7b, which illustrate precursor events during trapping, region denoted by 70, of 18F-fluoro-tetraacetyl-glucose (FTAG) on tC18 cartridge after labelling. By analysing historic data from multiple earlier runs in the trapping region, it is possible to identify behaviour that give an early warning signal for yield. In order to be able to compare historic data from different runs, the step of processing historic data may further comprises normalizing data from the multiple earlier runs on particular points. According to some embodiments, different analytic methods may be used to identify precursor events. These analytic methods include, but are not limited to, comparing time series, identifying Euclidean distance, clustering, etc. Similarity-based method requires less domain expertise but is less sensitive than feature based approach.

By adding up the total "loss" in each valley 71 and 72, a measure of tC18 activity loss may be established. The result of the analysis of historic data is that if the tC18 activity loss is high, then this is a result of poor labelling and thus low yield. Yield and loss are correlated, as illustrated in FIG. 5b.

Figure 8:
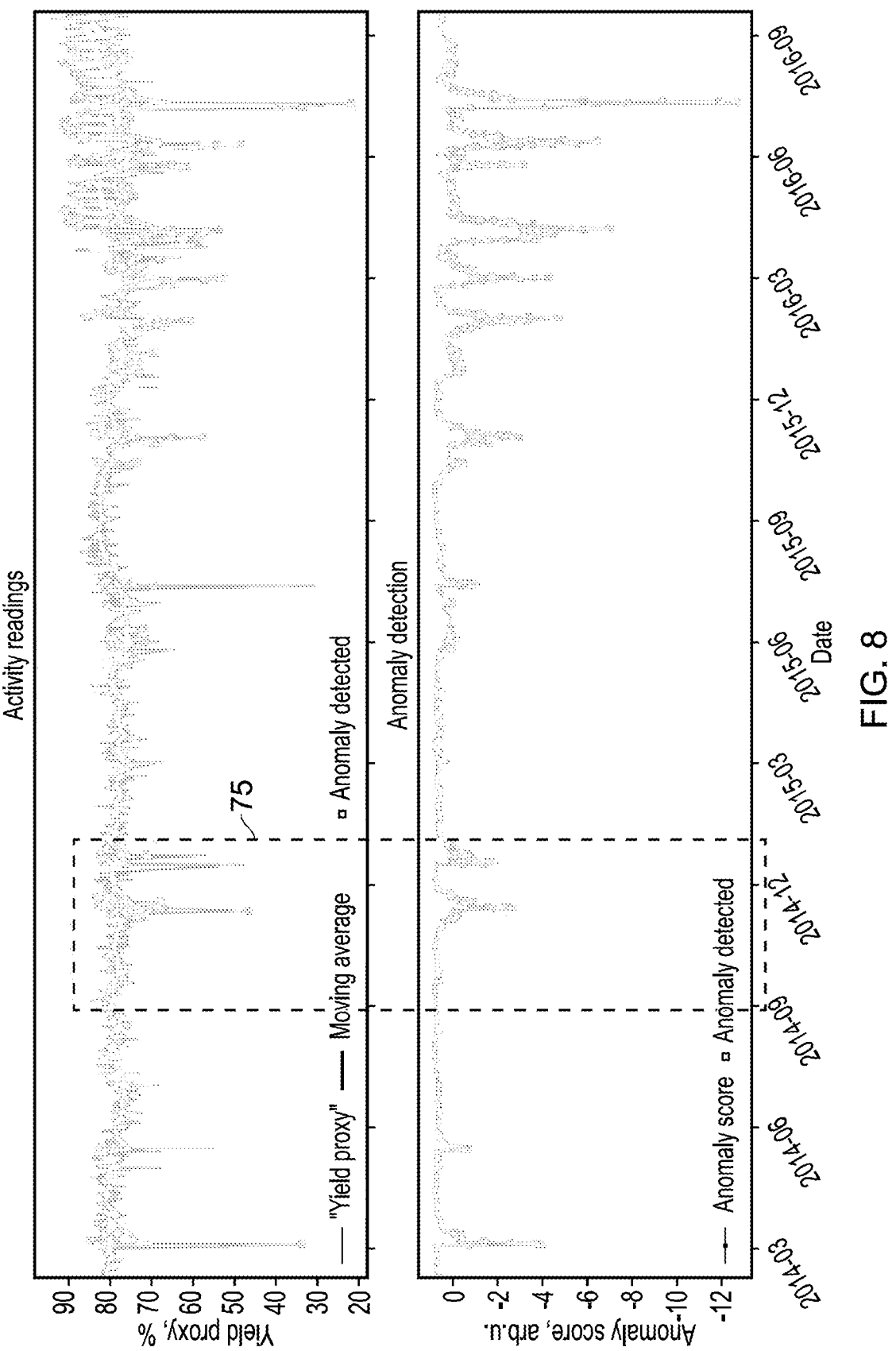
FIG. 8 illustrates a yield plot during a process run.

FIG. 8 illustrates a long time yield plot during a process run together with an anomaly detection curve. The long time yield plot includes raw data and rolling average—thick line. The anomalies are occasions during the process run, where the activity readings are deviating from what is expected (based on the historic data collected from earlier process runs). In this example, one region has been highlighted, 75. According to some embodiments, a model is created based on the historic data, and detecting the precursors of yield drop is performed by comparing the recorded activity data with the model.

Figure 9:
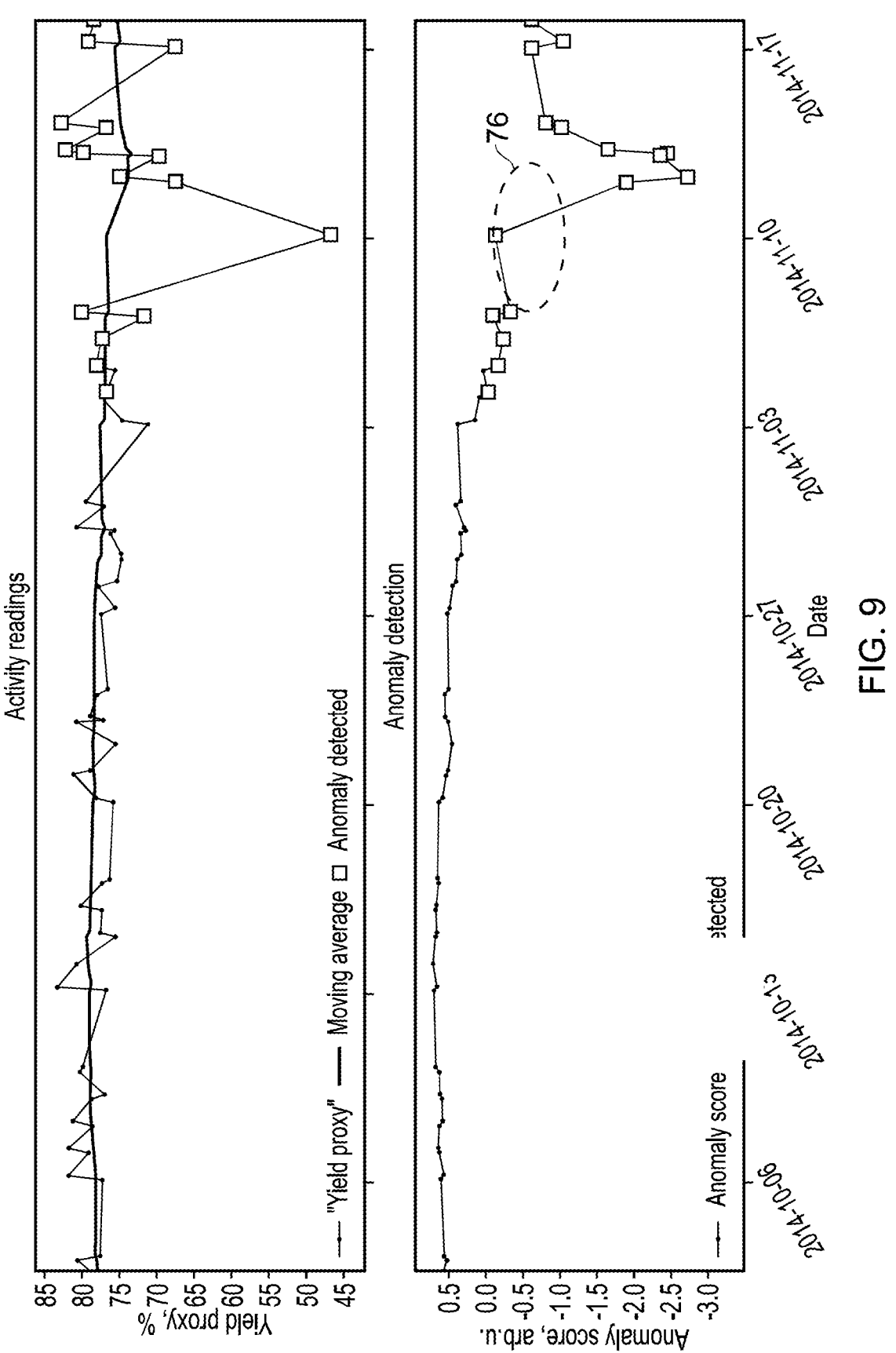
FIGS. 9 illustrates parts of the yield plot in FIG. 8 highlighting a first type of anomaly.

FIGS. 9 illustrates parts of the yield plot in FIG. 8 highlighting a first type of anomaly in region 75. The activity readings are used to detect anomalies, which results in an anomaly detection curve, lower curve in FIG. 9. In this example, the detected anomalies within the circle 78 is a precursor event that gives a warning signal and indicates that the yield is a risk. The yield may be predicted and actions related to a level of yield are recommended. According to some embodiments, actions is taken to maintain a desired output from the radiosynthesizer when the level of predicted yield is lower than a predetermined threshold. According to some embodiments, the automated radiosynthesizer has a production yield, e.g. 75%-85%, and the predetermined threshold is at least 10%, or 15%, lower than the production yield.

Examples of recommended actions when a yield drop is detected and the yield when synthesizing a tracer is predicted:

material is introduced into the automated radiosynthesizer when synthesizing the tracer, and the recommended action comprises adding more material.

the recommended actions relates to hardware issues and/or scheduled maintenance, e.g. maintenance is initiated before it the yield is below a predetermined level that is acceptable, such as 10%, or 15%, lower than the production yield.

There are several optional ways of detecting precursors of yield drop. A first option is to use "Single batch diagnostics", where deviating behaviour is detected. The deviations may be linked to trends. This has been exemplified for the labelling reactions in connection with FIGS. 6a, 6b, 7a and 7b. An example observation may include that the labelling reaction was sub-optimal giving the appearance of low FTAG trapping in the case of $^{18}$F-FDG synthesis. Yield will be sub-optimal.

This type of issue is most often caused by:
1. Quality parameters of [$^{18}$F]fluoride
2. FTAG trapping issue Further actions may be check performance vs other recent batches. Consider e.g. delivery line replacement.

A second option is to use "Yield advisor", where long term yield plot with raw data and rolling average is used. Maintenance events may also be included in the long term plot. Automatic anomaly detection, as illustrated in connection with FIGS. 8 and 9, may be used to give early warning signal that yield is at risk.

FIG. 10 illustrates a flowchart 80 of a batch browser process, which is a third option. The flow starts in 80, and a batch is selected in 81. If data from clusters or similar batches are going to be used, as indicated in 82, the flow continues to 83. On the other hand, if not, the flow continues to 84 where the selected batch is overlayed with historic data from chosen date ranges or specific batches.

In 83, characteristic features of the selected batch is specified to find clusters of similar batches, as indicated by 50 in FIG. 5a. The flow continues from 83 and 84 to 85, where the result is viewed. According to a first option 86, the result is presented as view trending for selected batch clusters, according to a second option 87, the result is presented as a timeline of when the batches occurred and overlay e.g. maintenance events.

In 88, actions are initiated to prevent yield drop based on the presented result in 85.

Different considerations regarding connectivity and deployment is contemplated, and this is reflected in different levels of connectivity.

Local

In a local version, the different options to detect precursors of yield drop and analytics required to predict yield based on the precursor of yield drop has to be installed locally on the radiosynthesizer as software. An advantage is minimal change to site operations. However, drawbacks is slow roll out of updates and inflexible.

Cloud

In the cloud based version, manual data is uploaded with web-based interface and a secure data storage is provided in the cloud. Advantages with a cloud based implementation are rapid customization, mobile and remote access, data back-up and a possibility to develop new features when data set grows. A disadvantage is that it is required to demonstrate security and privacy to the users of the system.

FIG. 11 illustrates a flowchart for monitoring an automated radiosynthesizer during a run, the radiosynthesizer having a number of individual activity detectors operably associated therewith.

Yield is an important parameter when producing tracers in a radiosynthesizer. If unexpected drop in yield occurs, the user of the system cannot prepare for this event. The purpose of this disclosure is not only to predict yield itself, but to detect precursors of yield drops. These precursors are linked to the underlying chemical process or hardware components used in the process.

Yield may be defined as the radioactivity remaining after the radiochemical synthesis divided by the radioactivity of the material entering the device. The exact definition may vary from user to user. Most users report that yield volatility is the main challenge, although absolute high yield is also important for some customers (the large scale commercial suppliers). It is important to improve yield where it has dropped by suggesting actions to achieve that.

Volatility in yield level what causes problem (at least for FDG). So the claim might be improve yield reliability.

In FIG. 11, the flow starts in step S1 and in step S10 activity data is recorded from each activity detector.

In step S20 historic data is accessed from a data storage. According to some embodiment the method further comprises selecting S22 the historic data to comprise data from earlier runs on the same radiosynthesizer. According to some embodiment the method further comprises selecting S24 the historic data further to comprise data from earlier runs on other radiosynthesizers.

According to some embodiments the method further comprises selecting S26 the data storage to be arranged externally to the radiosynthesizer, preferably in a cloud based implementation. According to some embodiments the method further comprises creating a model S28 based on the historic data, and detecting the precursors of yield drop by comparing the recorded activity data with the model. According to some embodiment a local data storage is arranged within the radiosynthesizer and the method further comprises storing S29 the model in the local data storage.

In step S30 precursor of yield drop is detected in the recorded activity data based on the historic data. According to some embodiments, the step of detecting precursors of yield drop comprises detecting anomalies S32. According to some embodiments the step of detecting the anomalies further comprises processing historic data S34 from multiple earlier runs to identify behaviour that give an early warning signal for yield. According to some embodiments, the step of processing historic data further comprises normalizing data from the multiple earlier runs on particular points.

According to some embodiment the step of detecting anomalies comprises fitting a mathematical function S36 to a selected region and evaluating the mathematical function based on its behaviour. according to some embodiments the mathematical function is selected to be:

$$y = 1 - Ae^{-\lambda t},$$

wherein y is the yield, A and $\lambda$ are constants and t is time, and the evaluation is based on the magnitude of $\lambda$.

According to some embodiments the step of detecting anomalies further comprises measuring a drop in yield S38 in the selected region.

In step S40, yield when synthesizing a tracer with the radiosynthesizer is predicted based on the detected precursor of yield drop; and in step S50 actions related to a level of predicted yield are initiated. The automated radiosynthesizer has a production yield that normally is in the range 75%-85%, i.e. remaining radioactivity in the output product divided by the radiativity of the input material. However, this number may vary depending on the type of tracer produced.

According to some embodiments the method further comprising initiating actions to maintain a desired output S52 from the radiosynthesizer when the level of predicted yield is lower than a predetermined threshold. According to some embodiments the automated radiosynthesizer has a production yield and the method further comprises selecting S54 the predetermined threshold to be at least 10% lower than the production yield. According to some embodiments the method further comprises selecting S56 the predetermined threshold to be at least 15% lower than the production yield. According to some embodiments material is introduced into the automated radiosynthesizer when synthesizing the tracer, and the action comprises adding more material. According to some embodiments the initiated actions relates to hardware issues and/or scheduled maintenance.

Additionally, monitoring of the automated radiosynthesizer may be performed automatically by a computer on board the synthesizer. That is, the present invention further contemplates providing a non-transitory computer-readable storage medium with an executable program for performing the steps for monitoring the radiosynthesizer, such that execution of the computer-readable program code causes a processor to perform the step of recording activity data from each activity detector, detecting precursors of yield drop in the recorded activity data based on historic data accessible from a data storage, predicting yield when synthesizing a tracer with the radiosynthesizer based on the detected precursors of yield drop; and recommending actions related to a level of predicted yield in a radiosynthesizer.

The present disclosure comprises a computer program for monitoring an automated radiosynthesizer during a run, comprising instructions which, when executed on at least one processor, cause the at least one processor to carry out the method described in connection with FIG. 11. Furthermore, the disclosure also comprises a computer-readable storage medium carrying the computer program for monitoring the automated radiosynthesizer.

The present disclosure also relates to a controller, as described in connection with FIGS. 3 and 4, for monitoring an automated radiosynthesizer during a run, the radiosynthesizer having a number of individual activity detectors operably associated therewith, wherein the control system is configured to:

recording activity data from each activity detector;

detecting precursors of yield drop in the recorded activity data based on historic data accessible from a data storage;

predicting yield when synthesizing a tracer with the radiosynthesizer based on the detected precursors of yield drop; and recommending actions related to a level of predicted yield.

According to some embodiments, the control system is configured to access an externally arranged data storage.

The invention claimed is:

1. A method of synthesizing a radiopharmaceutical using an automated radiosynthesizer during a run, the radiosynthesizer having a number of individual activity detectors operably associated therewith, comprising the steps of:

recording activity data from each activity detector;

accessing historic data from a data storage;

detecting precursors of yield drop in the recorded activity data based on the historic data, wherein the detecting precursors of yield drop comprises detecting anomalies by processing historic data from multiple earlier runs to identify behavior that give an early warning signal for yield, the processing of historic data comprises normalizing data from multiple earlier runs on particular points, fitting a mathematical function to the historic data for a selected region corresponding to the number of individual activity detectors and evaluating the mathematical function relative to the activity data, and the mathematical function is $y=1-Ae^{-\lambda t}$, wherein y is the yield, A and $\lambda$, are constants and t is time, and the evaluation is based on the magnitude of 2, where a $\lambda$, is indicative of precursors in yield drop;

predicting yield when synthesizing a tracer with the radiosynthesizer based on the detected precursors of yield drop; and initiating actions related to a level of predicted yield, where the precursor events are indicative of a radiolabelling reaction yield or a solid phase extraction cartridge trapping below a first predetermined threshold, and the initiating actions add more material to maintain an output from the radiosynthesizer based on the level of predicted yield being lower than a second predetermined threshold.

2. The method according to claim 1, wherein the automated radiosynthesizer has a production yield and the method further comprises selecting the second predetermined threshold to be at least 10% lower than the production yield.

3. The method according to claim 2, wherein the method further comprises selecting the second predetermined threshold to be at least 15% lower than the production yield.

4. The method according to claim 1, wherein material is introduced into the automated radiosynthesizer when synthesizing the tracer.

5. The method according to claim 1, wherein the initiated actions relate to hardware issues and/or scheduled maintenance.

6. The method according to claim 1, wherein the method further comprises selecting the historic data to comprise data from earlier runs on the same radiosynthesizer.

7. The method according to claim 6, wherein the method further comprises selecting the historic data to comprise data from earlier runs on other radiosynthesizers.

8. The method according to claim 1, wherein the method further comprises selecting the data storage to be arranged externally to the radiosynthesizer.

9. The method according to claim 1, wherein the method further comprises creating a model based on the historic data, and detecting the precursors of yield drop by comparing the recorded activity data with the model.

10. The method according to claim 9, wherein a local data storage is arranged within the radiosynthesizer and the method further comprises storing the model in the local data storage.

11. The method according to claim 1, wherein the step of detecting anomalies further comprises measuring a drop in yield in the selected region corresponding to the number of individual activity detectors.

12. A computer-implemented method program for monitoring an automated radiosynthesizer during a run, comprising instructions which, when executed on at least one processor, cause the at least one processor to carry out the method according to claim 1.

13. A non-transitory computer-readable storage medium carrying a computer program for monitoring an automated radiosynthesizer during a run according to claim 12.

14. A controller for synthesizing a pharmaceutical using an automated radiosynthesizer during a run, the radiosynthesizer having a number of individual activity detectors operable associated therewith, wherein the controller is configured to:

record activity data from each activity detector;

detect precursors of yield drop in the recorded activity data based on historic data accessible from a data storage, wherein the detecting precursors of yield drop comprises detecting anomalies by processing historic data from multiple earlier runs to identify behavior that give an early warning signal for yield, the processing of historic data comprises normalizing data from multiple earlier runs on particular points, fitting a mathematical function to the historic data for a selected region corresponding to each activity detector and evaluating the mathematical function relative to the activity data, and the mathematical function is $y=1-Ae-\lambda t$, wherein y is the yield, A and $\lambda$, are constants and t is time, and the evaluation is based on the magnitude of $\lambda$, where a $\lambda$, indicates precursors of yield drop;

predict yield when synthesizing a tracer with the radiosynthesizer based on the detected precursors of yield drop; and recommend actions related to a level of predicted yield, and where the precursor events are indicative of a radiolabelling reaction yield or a solid phase extraction cartridge trapping below a first predetermined threshold, and where initiating actions add more material to maintain an output from the radiosynthesizer when the level of predicted yield is lower than a second predetermined threshold.

15. The controller according to claim 14, wherein the controller is configured to access an externally arranged data storage.

16. A method of synthesizing a radiopharmaceutical using an automated radiosynthesizer during a run, the radiosynthesizer having a number of individual activity detectors operably associated therewith, comprising the steps of:

recording activity data from each activity detector;

accessing historic data from a data storage;

detecting precursors of yield drop in the recorded activity data based on the historic data, wherein the detecting precursors of yield drop comprises detecting anomalies by processing historic data from multiple earlier runs to identify behavior that give an early warning signal for yield, the processing of historic data comprises normalizing data from multiple earlier runs on particular points, fitting a mathematical function to the historic data for a selected region corresponding to the number of individual activity detectors and evaluating the mathematical function relative to the activity data, and the mathematical function is $y=1-Ae^{-\lambda t}$, wherein y is the yield, A and $\lambda$, are constants and t is time, and the evaluation is based on the magnitude of $\lambda$, where a $\lambda$, is indicative of precursors in yield drop;

predicting yield when synthesizing a tracer with the radiosynthesizer based on the detected precursors of yield drop; and initiating actions related to a level of predicted yield, where the precursor events are indicative of a radiolabelling reaction yield or a solid phase extraction cartridge trapping below a first predetermined threshold, and the initiating actions maintain an output from the radiosynthesizer based on the level of predicted yield being lower than a second predetermined threshold, wherein material is introduced into the automated radiosynthesizer when synthesizing the tracer, and the initiating actions comprise adding more material.

17. A controller for synthesizing a pharmaceutical using an automated radiosynthesizer during a run, the radiosynthesizer having a number of individual activity detectors operable associated therewith, wherein the controller is configured to:

record activity data from each activity detector;

detect precursors of yield drop in the recorded activity data based on historic data accessible from a data storage,

wherein the detecting precursors of yield drop comprises detecting anomalies by processing historic data from multiple earlier runs to identify behavior that give an early warning signal for yield, the processing of historic data comprises normalizing data from multiple earlier runs on particular points, fitting a mathematical function to the historic data for a selected region corresponding to each activity detector and evaluating the mathematical function relative to the activity data, and the mathematical function is $y=1-Ae-\lambda t$, wherein y is the yield, A and $\lambda$, are constants and t is time, and the evaluation is based on the magnitude of $\lambda$, where a $\lambda$, indicates precursors of yield drop;

predict yield when synthesizing a tracer with the radiosynthesizer based on the detected precursors of yield drop; and recommend actions related to a level of predicted yield, and where the precursor events are indicative of a radiolabelling reaction yield or a solid phase extraction cartridge trapping below a first predetermined threshold, and where initiating actions maintain an output from the radiosynthesizer when the level of predicted yield is lower than a second predetermined threshold, wherein material is introduced into the automated radiosynthesizer when synthesizing the tracer, and the initiating actions comprise adding more material.

* * * * *